(12) United States Patent
Paderi et al.

(10) Patent No.: US 9,173,919 B2
(45) Date of Patent: Nov. 3, 2015

(54) COLLAGEN-TARGETED NANOPARTICLES

(75) Inventors: John E. Paderi, San Francisco, CA (US); Alyssa Panitch, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 14/000,036

(22) PCT Filed: Feb. 16, 2012

(86) PCT No.: PCT/US2012/025431
§ 371 (c)(1),
(2), (4) Date: Aug. 16, 2013

(87) PCT Pub. No.: WO2012/112767
PCT Pub. Date: Aug. 23, 2012

(65) Prior Publication Data
US 2013/0323311 A1   Dec. 5, 2013

Related U.S. Application Data

(60) Provisional application No. 61/443,572, filed on Feb. 16, 2011, provisional application No. 61/488,385, filed on May 20, 2011.

(51) Int. Cl.
| | | |
|---|---|---|
| *A61K 38/10* | (2006.01) | |
| *A61K 47/48* | (2006.01) | |
| *A61K 49/00* | (2006.01) | |
| *A61K 49/04* | (2006.01) | |
| *B82Y 5/00* | (2011.01) | |
| *C07K 14/705* | (2006.01) | |
| *A61K 9/14* | (2006.01) | |

(52) U.S. Cl.
CPC ............... *A61K 38/10* (2013.01); *A61K 9/146* (2013.01); *A61K 47/48238* (2013.01); *A61K 47/48861* (2013.01); *A61K 47/48884* (2013.01); *A61K 47/48915* (2013.01); *A61K 49/0002* (2013.01); *A61K 49/0056* (2013.01); *A61K 49/0065* (2013.01); *A61K 49/0428* (2013.01); *B82Y 5/00* (2013.01); *C07K 14/7055* (2013.01)

(58) Field of Classification Search
CPC .................................................... A61K 38/10
See application file for complete search history.

(56) References Cited

U.S. PATENT DOCUMENTS

| | | | |
|---|---|---|---|
| 5,807,581 | A | 9/1998 | Rosenblatt et al. |
| 6,387,663 | B1 | 5/2002 | Hall et al. |
| 7,592,009 | B2 | 9/2009 | Hubbell et al. |
| 7,790,147 | B2 * | 9/2010 | Huang et al. .............. 424/61 |
| 8,304,388 | B2 * | 11/2012 | Chettibi et al. .............. 514/17.2 |
| 2002/0102709 | A1 | 8/2002 | Ishikawa et al. |
| 2009/0005298 | A1 * | 1/2009 | Goldberg et al. .............. 514/12 |
| 2009/0191123 | A1 * | 7/2009 | Chettibi et al. .............. 424/1.69 |
| 2009/0305352 | A1 * | 12/2009 | Dai et al. ...................... 435/69.7 |
| 2010/0129341 | A1 | 5/2010 | Sakon et al. |
| 2011/0020298 | A1 | 1/2011 | Panitch et al. |

FOREIGN PATENT DOCUMENTS

| | | | | |
|---|---|---|---|---|
| WO | WO 2007/138291 | * | 12/2007 | .............. A61K 49/00 |
| WO | WO 2009/120995 | * | 10/2009 | .............. A61K 38/16 |

OTHER PUBLICATIONS

Rothenfluh et al., 2008, Biofunctional polymer nanoparticles for intra-articular targeting and retention in cartilage, Nature Materials, 7: 248-254.*
Mo et al., 2006, Nanoparticle-Assisted Visualization of Binding Interactions between Collagen Mimetic peptide and Collagen Fibers, Angew. Chem. Int. Ed., 45: 2267-2270.*
Enochs et al., 1999, Improved Delineation of Human Brain Tumors on MR Images Using a Long-Circulating, Superparamagnetic Iron Oxide Agent, Journal of Magnetic Resonance Imaging, 9: 228-232.*
Garg et al., "Nanoparticles: A Review", (2007) Pharmaceutical Reviews 5(6), 26 pages.
Sounderya et al., "Use of Core/Shell Structured Nanoparticles for Biomedical Applications", (2008) Recent Patents on Biomedical Engineering 1:34-42.
Levy at el., "Rational and Combinational Design of Peptide Capping Ligands for Gold Nanoparticles", (2004) J. Am. Chem. Soc. 126: 10076-10084.
Jans et al. "Increased stability of mercapto alkane functionalized Au nanoparticles towards DNA sensing" (2010) Nanotechnology 21 : 1-8.
Cardenas et al. "Thiol-Specific and Nonspecific Interactions between DNA and Gold Nanoparticles", (2006) Langmuir 22: 3294-3299.
Chiang, et al "Peptides Derived from Platelet Non-integrin Collagen-receptors of Types I and III Collagen Inhibit Collagen-Platelet Interaction", (2007) Cardio. & Haemato. Disorders-Drug Targets 7: 71-75.
Chiang, et al., "Cloning Characterization, and Functional Studies of a 47-kDa Platelet Receptor for Type III Collagen", (2002) J. Biol. Chem. 277: 34896-34901.
Huizinga, et al., "Crystal structure of the A3 domain of human von Willebrand factor: implications for collagen binding", (1997) Structure 5: 1147-1156.
Romijn, et al., "Mapping the Collagen-binding Site in the von Willebrand Factor-A3 Domain", (2003) J. Biol. Chem. 278: 15035-15039.
Jeong et al., "A Novel Assay to Probe Heparin-Peptide Interactions Using Pentapeptide-Stabilized Gold Nanoparticles", (2008) Langmuir (16): 8794-8800.

(Continued)

*Primary Examiner* — Amber D Steele
(74) *Attorney, Agent, or Firm* — Sheppard Mullin Richter & Hampton LLP

(57) ABSTRACT

This invention relates to compositions comprising collagen binding peptides coupled to nanoparticles. The invention also relates to a method of imaging a collagenous matrix using a composition comprising collagen binding peptides coupled to nanoparticles.

18 Claims, 9 Drawing Sheets

(56) References Cited

OTHER PUBLICATIONS

Storhoff et al., "One-Pot Colorimetric Differentiation of Polynucleotides with Single Base Imperfections Using Gold Nanoparticle Probes", (1998) JACS 120(9): 1959-1964.

Liu et al., "Synthesis, Stability, and Cellular Internalization of Gold Nanoparticles Containing Mixed Peptide-Poly(ethylene glycol) Monolayers", (2007) Analytical Chem. 79(6): 2221-2229.

Rothenfluh et al., "Biofunctional polymer nanoparticles for intra-articular targeting and retention in cartilage", (2008) Nature Materials 7: 248-254.

Haidekker et al., "Influence of gold nanoparticles on collagen fibril morphology quantified using transmission electron microscopy and image analysis", (2006) BMC Medical Imaging 6: 1-7.

PCT Search Report and Written Opinion for PCT/US2012/025431, completed Aug. 29, 2012.

* cited by examiner

SEQUENCE LISTING

```
<160> NUMBER OF SEQ ID NOS: 34

<210> SEQ ID NO 1
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Arg Ala Asn Ala Ala Leu Lys Ala Gly Glu Leu Tyr Lys Ser Ile
1               5                   10                  15

Leu Tyr

<210> SEQ ID NO 2
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Arg Ala Asn Ala Ala Leu Lys Ala Gly Glu Leu Tyr Lys Cys Ile
1               5                   10                  15

Leu Tyr

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Glu Leu Tyr Lys Ser Ile Leu Tyr
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Glu Leu Tyr Lys Cys Ile Leu Tyr
1               5

<210> SEQ ID NO 5
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 5

Ser Tyr Ile Arg Ile Ala Asp Thr Asn Ile Thr
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Lys Lys Thr Leu Arg Thr
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Gln Asn Pro Val Gln Pro
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Leu Asp Gly Asn Glu Ile Lys Arg
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Glu Leu Asn Val Tyr Thr
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Leu Trp Val Leu Pro Lys
1               5
```

```
<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys Gln Asp Ser Glu Thr Arg Thr Phe Tyr
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala His Glu Glu Ile Ser Thr Thr Asn Glu Gly Val Met
1               5                   10

<210> SEQ ID NO 13
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Leu Arg Ser Lys Ser Lys Lys Phe Arg Arg Pro Asp Ile Gln Tyr
1               5                   10                  15

Pro Asp Ala Thr Asp Glu Asp Ile Thr Ser His Met
            20                  25

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Ser Ile Thr Thr Ile Asp Val Pro Trp Asn Val
1               5                   10

<210> SEQ ID NO 15
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asn Gly Val Phe Lys Tyr Arg Pro Arg Tyr Phe Leu Tyr Lys His Ala
1               5                   10                  15

Tyr Phe Tyr Pro Pro Leu Lys Arg Phe Pro Val Gln
            20                  25
```

```
<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser, Cys or Thr

<400> SEQUENCE: 16

Gly Glu Leu Tyr Lys Xaa Ile Leu Tyr
1               5

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Ile Leu Tyr
1

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Cys Ala Leu Asn Asn
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Trp Tyr Arg Gly Arg Leu Cys
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Trp Tyr Arg Gly Arg Leu Gly Cys
1               5

<210> SEQ ID NO 21
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 21

Ala His Glu Glu Ile Ser Thr Thr Asn Glu Gly Val Met Gly Cys
1               5                   10                  15

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Leu Asp Gly Asn Glu Ile Lys Arg Gly Cys
1               5                   10

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Lys Lys Thr Leu Arg Thr Gly Cys
1               5

<210> SEQ ID NO 24
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gly Leu Arg Ser Lys Ser Lys Lys Phe Arg Arg Pro Asp Ile Gln Tyr
1               5                   10                  15

Pro Asp Ala Thr Asp Glu Asp Ile Thr Ser His Met Gly Cys
            20                  25                  30

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Gln Asn Pro Val Gln Pro Gly Cys
1               5

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 26

Ser Tyr Ile Arg Ile Ala Asp Thr Asn Ile Thr Gly Cys
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Glu Leu Asn Leu Val Tyr Thr Gly Cys
1               5                   10

<210> SEQ ID NO 28
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asn Gly Val Phe Lys Tyr Arg Pro Arg Tyr Phe Leu Tyr Lys His Ala
1               5                   10                  15

Tyr Phe Tyr Pro Pro Leu Lys Arg Phe Pro Val Gln Gly Cys
            20                  25                  30

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Ser Ile Thr Thr Ile Asp Val Pro Trp Asn Val Gly Cys
1               5                   10

<210> SEQ ID NO 30
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Arg Ala Asn Ala Ala Leu Lys Ala Gly Glu Leu Tyr Lys Ser Ile
1               5                   10                  15

Leu Tyr Gly Cys
            20

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 31

Gly Glu Leu Tyr Lys Ser Ile Leu Tyr Gly Cys
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Cys Gly Gly Glu Leu Tyr Lys Ser Ile Leu Tyr
1               5                   10

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Tyr-biotin

<400> SEQUENCE: 33

Ser Ile Leu Tyr
1

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Biotin-Trp

<400> SEQUENCE: 34

Trp Tyr Arg Gly Arg Leu Cys
1               5
```

COLLAGEN-TARGETED NANOPARTICLES

CROSS REFERENCE TO RELATED APPLICATIONS

This application is a national stage entry under 35 USC §371(b) of International Application No. PCT/US2012/025431, filed Feb. 16, 2012, which claims the benefit under 35 USC §119(e) of U.S. Provisional Application Ser. No. 61/443,572 filed on Feb. 16, 2011 and U.S. Provisional Application Ser. No. 61/488,385 filed on May 20, 2011 the entire disclosures of which are incorporated herein by reference.

SEQUENCE LISTING

The instant application contains a Sequence Listing which has been submitted electronically in ASCII format and is hereby incorporated by reference in its entirety. Said ASCII copy, created on Jul. 30, 2014, is named 3220E-226330_SL.txt and is 9,221 bytes in size.

TECHNICAL FIELD

This invention generally pertains to the field of nanomedicine. More particularly, the invention pertains to collagen-binding peptides coupled to nanoparticles.

BACKGROUND AND SUMMARY OF THE INVENTION

Nanoparticles are submicron materials that often possess different properties than bulk material of the same kind. Nanoparticles have been studied for uses in many fields, including diagnostic and therapeutic applications in the life sciences. Because of their small size and unique properties, nanoparticles often have enhanced distribution in the body compared to larger sized particles. Further, nanoparticles may be specifically directed to particular targets in the body by attaching one or more components to the nanoparticle surface (i.e. functionalization). Functionalization of a nanoparticle with a component having affinity for a specific target in the body, for example, collagen, can direct the nanoparticle to tissues containing the target molecule.

There are more than 20 types of collagen currently identified, with type I being the most common. Many tissues are composed primarily of type I collagen including tendon, ligament, skin, and bone. While each of these structures also contains other collagen types, proteoglycans and glycosaminoglycans, and minerals in the case of bone, the principle component is type I collagen.

Disclosed herein is targeted delivery of nanoparticles, utilizing collagen as an attachment site for functionalized nanoparticles. Collagens are a component of the extracellular matrix (ECM), which is responsible for supporting cells, thus making up connective tissues such as blood vessels, cartilage, or skin. Collagens and their corresponding binding domains have been well studied. Collagen binding domains can be reduced to specific peptide sequences, which bind specifically and exclusively to collagen, the target protein. Utilizing peptide synthesis, it is possible to immobilize a collagen-binding peptide, for example a collagen type I or type II binding peptide, onto nanoparticles, allowing those nanoparticles to fasten specifically to type I or type II collagen, respectively.

This targeted delivery system is not limited to type I collagen, as many other collagen types have also been defined. As such, specific targeting of a variety connective tissues and proteins is also contemplated. Collagen-binding gold nanoparticles, for example, are useful for a variety of biomedical imaging techniques including SEM, TEM, confocal microscopy, MRI, and photoacoustic imaging. Further, radiopaque nanoparticles that are coupled with collagen binding proteins can be used in radiologic imaging such as CT scan or X-ray.

The following various embodiments are contemplated:

1) A composition comprising at least one collagen binding polypeptide coupled to a nanoparticle, wherein the polypeptide contains from 7 amino acids to 40 amino acids and wherein the polypeptide does not form a triple helix.

2) The composition of clause 1 wherein the nanoparticle further comprises a stabilizer.

3) The composition of clause 2 wherein the stabilizer is selected from the group consisting of a polyethylene glycol (PEG), a dextran, a peptide, an alkane-thiol, and an oligonucleotide-thiol.

4) The composition of clause 3 wherein the stabilizer is PEG.

5) The composition of any of clauses 1 to 4 wherein the polypeptide contains from 9 amino acids to 40 amino acids.

6) The composition of any of clauses 1 to 4 wherein the polypeptide contains from 9 amino acids to 30 amino acids.

7) The composition of any of clauses 1 to 4 wherein the polypeptide contains from 9 amino acids to 18 amino acids.

8) The composition of any of clauses 1 to 4 wherein the polypeptide is selected from the group consisting of RRANAALKAGELYKSILY (SEQ ID NO: 1), RRANAALKAGELYKCILY (SEQ ID NO: 2), GELYKSILY (SEQ ID NO: 3), GELYKCILY (SEQ ID NO: 4), SYIRIADTNIT (SEQ ID NO: 5), TKKTLRT (SEQ ID NO: 6), SQNPVQP (SEQ ID NO: 7), RLDGNEIKR (SEQ ID NO: 8), KELNVYT (SEQ ID NO: 9), KLWVLPK (SEQ ID NO: 10), CQDSETRTFY (SEQ ID NO: 11), AHEEISTTNEGVM (SEQ ID NO: 12), GLRSKSKKFRRPDIQYPDATDEDITSHM (SEQ ID NO: 13), GSITTIDVPWNV (SEQ ID NO: 14), and NGVFKYRPRYFLYKHAYFYPPLKRFPVQ (SEQ ID NO: 15).

9) The composition of any of clauses 1 to 4 wherein the polypeptide is selected from the group consisting of RRANAALKAGELYKSILY (SEQ ID NO: 1), RRANAALKAGELYKCILY (SEQ ID NO: 2), GELYKSILY (SEQ ID NO: 3), GELYKCILY (SEQ ID NO: 4), SYIRIADTNIT (SEQ ID NO: 5), TKKTLRT (SEQ ID NO: 6), SQNPVQP (SEQ ID NO: 7), and RLDGNEIKR (SEQ ID NO: 8).

10) The composition of any of clauses 1 to 4 wherein the polypeptide comprises the amino acid sequence GELYKXILY, wherein X is serine, cysteine, or threonine (SEQ ID NO: 16).

11) The composition of any of clauses 1 to 4 wherein the polypeptide is RRANAALKAGELYKSILY (SEQ ID NO: 1).

12) The composition of any of clauses 1 to 4 wherein the polypeptide is RRANAALKAGELYKCILY (SEQ ID NO: 2).

13) The composition of any of clauses 1 to 12 further comprising a cysteine at the amino terminal region or carboxy terminal region.

14) The composition of clause 13 further comprising a spacer.

15) The composition of clause 14 wherein the spacer comprises at least one glycine.

16) The composition of any of clauses 1 to 12 further comprising a peptide sequence selected from the group consisting of GC, CG, and GCG.

17) The composition of any of clauses 1 to 16 wherein the nanoparticle is a polymeric nanoparticle, a metallic nanoparticle, a semiconductor nanoparticle, or any combination thereof.

18) The composition of clause 17 wherein the nanoparticle is a gold nanoparticle.

19) The composition of clause 17 wherein the nanoparticle is an iron oxide nanoparticle.

20) The composition of any of clauses 1 to 19 further comprising a carrier.

21) The composition of clause 20 wherein the carrier is a pharmaceutically acceptable carrier.

22) The composition of clause 21 wherein the carrier is a liquid carrier and is selected from the group consisting of saline, glucose, alcohols, glycols, esters, amides, and a combination thereof.

23) An effective dose of the composition of any of clauses 1 to 22 for administration to a patient, wherein the effective dose ranges from about 1 ng to about 1 mg per kilogram of body weight.

24) An effective dose of the composition of any of clauses 1 to 22 for administration to a patient, wherein the effective dose ranges from about 1 pg to about 10 ng per kilogram of body weight.

25) An effective dose of the composition of any of clauses 1 to 22 for administration to a patient, wherein the effective dose ranges from about 1 µg to about 100 µg per kilogram of body weight.

26) A composition for use in imaging a collagenous matrix, the composition comprising at least one collagen binding polypeptide coupled to a nanoparticle, wherein the polypeptide contains from 7 amino acids to 40 amino acids and wherein the polypeptide does not form a triple helix.

27) The composition of clause 26 wherein the nanoparticle further comprises a stabilizer.

28) The composition of clause 27 wherein the stabilizer is selected from the group consisting of a polyethylene glycol (PEG), a dextran, a peptide, an alkane-thiol, and an oligonucleotide-thiol.

29) The composition of clause 28 wherein the stabilizer is PEG.

30) The composition of any of clauses 26 to 29 wherein the polypeptide contains from 9 amino acids to 40 amino acids.

31) The composition of any of clauses 26 to 29 wherein the polypeptide contains from 9 amino acids to 30 amino acids.

32) The composition of any of clauses 26 to 29 wherein the polypeptide contains from 9 amino acids to 18 amino acids.

33) The composition of any of clauses 26 to 29 wherein the polypeptide is selected from the group consisting of RRANAALKAGELYKSILY (SEQ ID NO: 1), RRANAALKAGELYKCILY (SEQ ID NO: 2), GELYKSILY (SEQ ID NO: 3), GELYKCILY (SEQ ID NO: 4), SYIRIADTNIT (SEQ ID NO: 5), TKKTLRT (SEQ ID NO: 6), SQNPVQP (SEQ ID NO: 7), RLDGNEIKR (SEQ ID NO: 8), KELNVYT (SEQ ID NO: 9), KLWVLPK (SEQ ID NO: 10), CQDSETRTFY (SEQ ID NO: 11), AHEEISTTNEGVM (SEQ ID NO: 12), GLRSKSKKFRRPDIQYPDATDEDITSHM (SEQ ID NO: 13), GSITTIDVPWNV (SEQ ID NO: 14), and NGVFKYRPRYFLYKHAYFYPPLKRFPVQ (SEQ ID NO: 15).

34) The composition of any of clauses 26 to 29 wherein the polypeptide is selected from the group consisting of RRANAALKAGELYKSILY (SEQ ID NO: 1), RRANAALKAGELYKCILY (SEQ ID NO: 2), GELYKSILY (SEQ ID NO: 3), GELYKCILY (SEQ ID NO: 4), SYIRIADTNIT (SEQ ID NO: 5), TKKTLRT (SEQ ID NO: 6), SQNPVQP (SEQ ID NO: 7), and RLDGNEIKR (SEQ ID NO: 8).

35) The composition of any of clauses 26 to 29 wherein the polypeptide comprises the amino acid sequence GELYKXILY, wherein X is serine, cysteine, or threonine (SEQ ID NO: 16).

36) The composition of any of clauses 26 to 29 wherein the polypeptide is RRANAALKAGELYKSILY (SEQ ID NO: 1).

37) The composition of any of clauses 26 to 29 wherein the polypeptide is RRANAALKAGELYKCILY (SEQ ID NO: 2).

38) The composition of any of clauses 26 to 37 further comprising a cysteine at the amino terminal region or carboxy terminal region.

39) The composition of clause 38 further comprising a spacer.

40) The composition of clause 39 wherein the spacer comprises at least one glycine.

41) The composition of any of clauses 26 to 37 further comprising a peptide sequence selected from the group consisting of GC, CG, and GCG 42) The composition of any of clauses 26 to 41 wherein the nanoparticle is a polymeric nanoparticle, a metallic nanoparticle, a semiconductor nanoparticle, or any combination thereof.

43) The composition of clause 42 wherein the nanoparticle is a gold nanoparticle.

44) The composition of clause 42 wherein the nanoparticle is an iron oxide nanoparticle.

45) The composition of any of clauses 26 to 44 further comprising a carrier.

46) The composition of clause 45 wherein the carrier is a pharmaceutically acceptable carrier.

47) The composition of clause 46 wherein the carrier is a liquid carrier and is selected from the group consisting of saline, glucose, alcohols, glycols, esters, amides, and a combination thereof.

48) An effective dose of the composition of any of clauses 26 to 47 for administration to a patient, wherein the effective dose ranges from about 1 ng to about 1 mg per kilogram of body weight.

49) An effective dose of the composition of any of clauses 26 to 47 for administration to a patient, wherein the effective dose ranges from about 1 pg to about 10 ng per kilogram of body weight.

50) An effective dose of the composition of any of clauses 26 to 47 for administration to a patient, wherein the effective dose ranges from about 1 µg to about 100 µg per kilogram of body weight.

51) A method for imaging a collagenous matrix, the method comprising the steps of contacting a collagenous matrix with a composition comprising at least one collagen binding polypeptide coupled to a nanoparticle, wherein the polypeptide contains from 7 amino acids to 40 amino acids and wherein the polypeptide does not form a triple helix, and imaging the collagenous matrix.

52) The method of clause 51 wherein the nanoparticle further comprises a stabilizer.

53) The method of clause 52 wherein the stabilizer is selected from the group consisting of a polyethylene glycol (PEG), a dextran, a peptide, an alkane-thiol, and an oligonucleotide-thiol.

54) The method of clause 53 wherein the stabilizer is PEG.

55) The method of any of clauses 51 to 54 wherein the polypeptide contains from 9 amino acids to 40 amino acids.

56) The method of any of clauses 51 to 54 wherein the polypeptide contains from 9 amino acids to 30 amino acids.

57) The method of any of clauses 51 to 54 wherein the polypeptide contains from 9 amino acids to 18 amino acids.

58) The method of any of clauses 51 to 54 wherein the polypeptide is selected from the group consisting of RRANAALKAGELYKSILY (SEQ ID NO: 1), RRANAALKAGELYKCILY (SEQ ID NO: 2), GELYKSILY (SEQ ID NO: 3), GELYKCILY (SEQ ID NO: 4), SYIRIADTNIT (SEQ ID NO: 5), TKKTLRT (SEQ ID NO: 6), SQNPVQP (SEQ ID NO: 7), RLDGNEIKR (SEQ ID NO: 8), KELNVYT (SEQ ID NO: 9), KLWVLPK (SEQ ID NO: 10), CQDSETRTFY (SEQ ID NO: 11), AHEEISTTNEGVM (SEQ ID NO: 12), GLRSKSKKFRRPDIQYPDATDEDITSHM (SEQ ID NO: 13), GSITTIDVPWNV (SEQ ID NO: 14), and NGVFKYRPRYFLYKHAYFYPPLKRFPVQ (SEQ ID NO: 15).

59) The method of any of clauses 51 to 54 wherein the polypeptide is selected from the group consisting of RRANAALKAGELYKSILY (SEQ ID NO: 1), RRANAALKAGELYKCILY (SEQ ID NO: 2), GELYKSILY (SEQ ID NO: 3), GELYKCILY (SEQ ID NO: 4), SYIRIADTNIT (SEQ ID NO: 5), TKKTLRT (SEQ ID NO: 6), SQNPVQP (SEQ ID NO: 7), and RLDGNEIKR (SEQ ID NO: 8).

60) The method of any of clauses 51 to 54 wherein the polypeptide comprises the amino acid sequence GELYKXILY, wherein X is serine, cysteine, or threonine (SEQ ID NO: 16).

61) The method of any of clauses 51 to 54 wherein the polypeptide is RRANAALKAGELYKSILY (SEQ ID NO: 1).

62) The method of any of clauses 51 to 54 wherein the polypeptide is RRANAALKAGELYKCILY (SEQ ID NO: 2).

63) The composition of any of clauses 51 to 62 further comprising a cysteine at the amino terminal region or carboxy terminal region.

64) The composition of clause 63 further comprising a spacer.

65) The composition of clause 64 wherein the spacer comprises at least one glycine.

66) The composition of any of clauses 51 to 62 further comprising a peptide sequence selected from the group consisting of GC, CG, and GCG.

67) The method of any of clauses 51 to 66 wherein the nanoparticle is a polymeric nanoparticle, a metallic nanoparticle, a semiconductor nanoparticle, or any combination thereof.

68) The method of clause 67 wherein the nanoparticle is a gold nanoparticle.

69) The method of clause 67 wherein the nanoparticle is an iron oxide nanoparticle.

70) The method of any of clauses 51 to 69 further comprising a carrier.

71) The method of clause 70 wherein the carrier is a pharmaceutically acceptable carrier.

72) The method of clause 71 wherein the carrier is a liquid carrier and the liquid carrier is selected from the group consisting of saline, glucose, alcohols, glycols, esters, amides, and a combination thereof.

73) The method of any of clauses 51 to 72 wherein an effective dose is administered to a patient, the effective dose ranging from about 1 ng to about 1 mg per kilogram of body weight.

74) The method of any of clauses 51 to 72 wherein an effective dose is administered to a patient, the effective dose ranging from about 1 pg to about 10 ng per kilogram of body weight.

75) The method of any of clauses 51 to 72 wherein an effective dose is administered to a patient, the effective dose ranging from about 1 µg to about 100 µg per kilogram of body weight.

76) The composition or method of any of clauses 1 to 75 wherein the polypeptide is coupled to the nanoparticle using a crosslinking agent.

BRIEF DESCRIPTION OF THE DRAWINGS

FIG. 1 discloses 'SILY' as SEQ ID NO: 17.

FIG. 4 discloses 'WYRGRLGC' as SEQ ID NO: 20.

DETAILED DESCRIPTION OF THE ILLUSTRATIVE EMBODIMENTS

Figure 1:
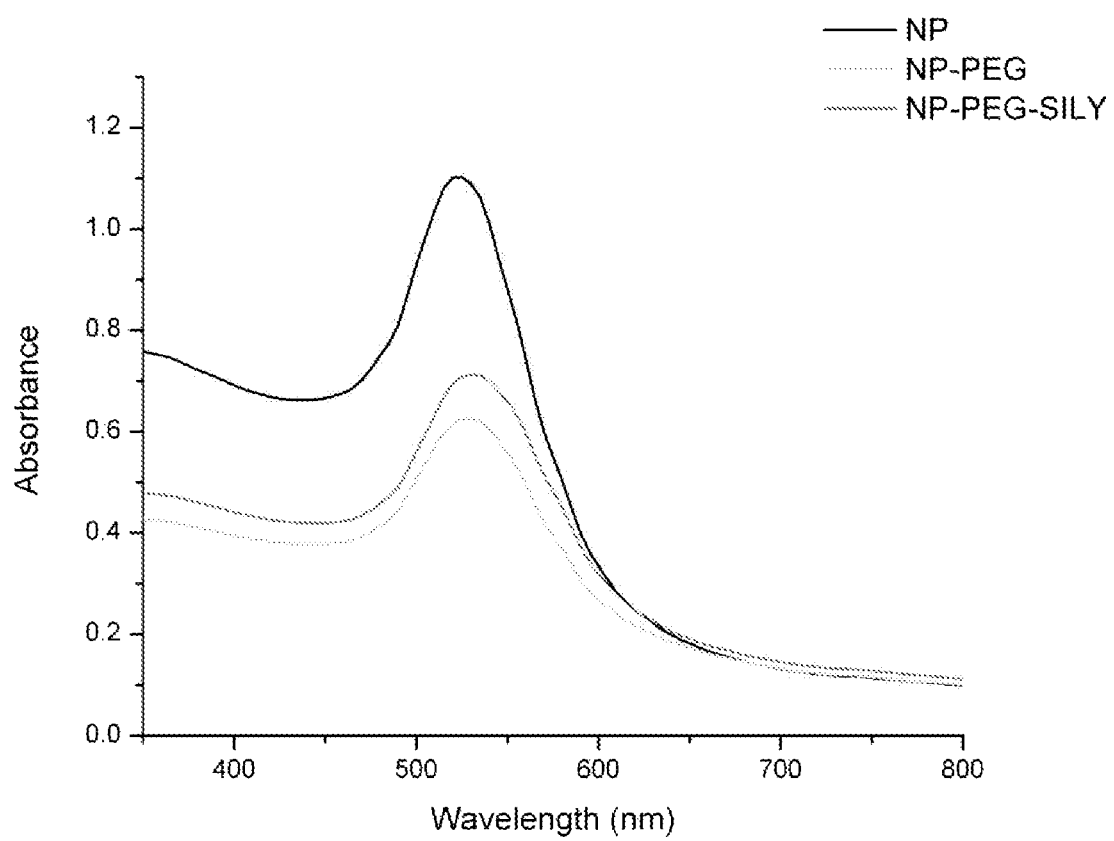
FIG. 1. Stability of functionalized nanoparticles (NP). NP functionalized with polyethylene glycol (PEG) are stable in 1×PBS as shown by the absorbance spectrum in which the maximum absorbance appears around 525 nm and immediately drops off as in the NP control. Likewise, after coupling SILY (SEQ ID NO: 17) to the PEG functionalized NP, stability is maintained. There is a slight shift in maximum absorbance from 522 nm to approximately 530 nm which indicates an increase in particle size consistent with coupling of PEG and SILY (SEQ ID NO: 17).

As used herein, a "collagen binding peptide" means a polypeptide that binds to one or more types of collagen.

As used herein the terms "nanoparticle coupled collagen binding peptide" and "collagen binding peptide(s) coupled to a nanoparticle(s)" are used interchangeably and refer to one or more collagen binding peptides coupled to one or more nanoparticles.

As used herein "collagenous matrix" refers to a tissue or component thereof that contains one or more types of collagen.

A nanoparticle is understood by those of skill in the art to refer to a particle having at least one dimension of submicron size. Nanoparticles may be composed from one or more of several types of materials, for example polymers [e.g., Poly (lactic-co-glycolic acid) (PLGA) or poly(N-isopropylacrylamide) (pNIPAM)], metals, semiconductors, and the like. Exemplary nanoparticles are gold nanoparticles and iron oxide nanoparticles. For a review see Garg et al. (2007) *Pharmaceutical Reviews* 5(6), available at www.pharmainfo.net/reviews/nanoparticles-review, incorporated herein by reference.

The nanoparticles may also be composed of a combination of material types, for example, as a core/shell structure. Core/shell nanoparticles are nanostructures that have a core made of a material coated with another material. For review of core/shell nanostructures see Zhang et al. (2008) *Recent Patents on Biomedical Engineering* 1:34-42, incorporated herein by reference. Illustratively, a core/shell nanoparticle may have a core and shell comprising one or more of several types of materials, for example polymers (e.g., PLGA and/or pNIPAM), metals (e.g., gold), semiconductors, and the like. In one illustrative embodiment, the core/shell nanoparticle may have a core comprising, for example, iron oxide and a shell comprising gold. In one illustrative embodiment, the core/shell nanoparticle may have a core comprising, for example, PLGA and a shell comprising pNIPAM.

In various embodiments, the nanoparticles described herein can have at least one dimension of about 1 nm to about 700 nm, about 1 nm to about 500 nm, about 1 nm to about 250 nm, about 100 nm to about 700 nm, about 100 nm to about 500 nm, about 100 to about 250 nm, about 250 to about 700 nm, about 250 to about 500 nm, or about 500 nm to about 700 nm. In various embodiments, the nanoparticles described herein can have at least one dimension of about 1 nm to about 100 nm, about 1 nm to about 10 nm, about 1 nm to about 20 nm, about 1 nm to about 30 nm, about 1 nm to about 40 nm, about 1 nm to about 50 nm, about 1 nm to about 60 nm, about 1 nm to about 70 nm, about 1 nm to about 80 nm, or about 1 nm to about 90 nm. In various embodiments, the nanoparticles described herein can have at least one dimension of about 30 nm to about 100 nm, about 40 nm to about 100 nm, about 50 nm to about 100 nm, about 60 nm to about 100 nm, about 20 nm to about 80 nm, about 30 nm to about 50 nm, or about 20 nm to about 50 nm. These various nanoparticle size ranges are also contemplated where the term "about" is not included.

In one illustrative embodiment, the nanoparticle is coupled to a "stabilizer." A stabilizer, for example, can inhibit or can prevent aggregation of the nanoparticles. Illustrative examples of stabilizers include, but are not limited to, a polyethylene glycol (PEG), a dextran, a peptide, an alkane-thiol, and an oligonucleotide-thiol. Peptide stabilizers, for example, those having the amino acid sequence CALNN (SEQ ID NO: 18) and its derivatives, are described by Levi at el. (2004) *J. Am. Chem. Soc.* 126: 10076-10084, incorporated herein by reference. Alkane-thiols and oligonucleotide-thiols are described by Jans et al. (2010) *Nanotechnology* 21: 1-8 and Cardenas et al. (2006) *Langmuir* 22: 3294-3299, respectively, each of which is incorporated herein by reference. The molecular weight of the stabilizer may be varied according to the size of the coupled polypeptides to effectively maintain stability of the nanoparticle with minimal interference in specific binding of the polypeptide to its target.

In one illustrative embodiment described herein are compositions comprising at least one collagen binding polypeptide coupled to a nanoparticle, wherein the polypeptide contains from 7 to 40 amino acid residues and wherein the polypeptide does not form a triple helix. A triple helix, for example, a collagen triple helix, is a quaternary structure containing three left-handed helices twisted together. Illustratively, a peptide with repeating units of a sequence of Z-Z-G, wherein Z is any amino acid and G is glycine, is a typical peptide motif that forms a triple helix. Specifically, collagen mimetics, such as, for example, a peptide comprising repeating units of Proline-Hydroxyproline-Glycine, are exemplary of a peptide that forms a triple helix.

As used in accordance with this invention, "nanoparticle coupled collagen binding peptides" refers to one or more collagen binding peptides coupled to one or more nanoparticles. In one illustrative aspect, a nanoparticle is coupled to a collagen binding peptide that binds a single type of collagen (for example, such as collagen type I, or type II, or type III, or type IV, or type V to type XXIX). In another illustrative aspect, a nanoparticle is coupled to a collagen binding peptide that binds multiple types of collagen (i.e. is not specific for a single collagen type). In another illustrative aspect, a nanoparticle is coupled to multiple copies of the same collagen binding peptide. In another illustrative aspect, a nanoparticle is coupled to one or more collagen binding peptides that differ in their specificity for binding to collagen types.

In various illustrative embodiments, the collagen binding peptides may bind to any type of collagen, including collagen types I to XXIX, alone or in any combination, for example, collagen types I, II (e.g., WYRGRLC (SEQ ID NO: 19) and WYRGRLGC (SEQ ID NO: 20)), III, and/or IV. In various illustrative aspects, the composition comprising collagen binding peptides coupled to a nanoparticle comprises collagen binding peptides of about 7 to about 40 amino acids. In one illustrative aspect, the composition comprising collagen binding peptides coupled to a nanoparticle comprises collagen binding peptides of about 7 to about 35 amino acids, or from about 7 to about 30 amino acids, from about 7 to about 25 amino acids, from about 7 to about 22 amino acids, from about 7 to about 18 amino acids, from about 7 to about 15 amino acids, from about 9 to about 40 amino acids, from about 9 to about 18 amino acids, from about 15 to about 30 amino acids, or from about 15 to about 25 amino acids. In various illustrative aspects, the composition comprising collagen binding peptides coupled to a nanoparticle comprises collagen binding peptides of about 7 to about 50 or about 60 amino acids.

These various peptide amino acid ranges are also contemplated where the term "about" is not included. For example, the composition comprising collagen binding peptides coupled to a nanoparticle can comprise collagen binding peptides of 7 amino acids to 20 amino acids, 7 amino acids to 35 amino acids, or from 7 amino acids to 30 amino acids, from 7 amino acids to 25 amino acids, from 7 amino acids to 22 amino acids, from 7 amino acids to 18 amino acids, from 7 amino acids to 15 amino acids, from 9 amino acids to 40 amino acids, from 9 amino acids to 18 amino acids, from 15 amino acids to 30 amino acids, or from 15 amino acids to 25 amino acids.

In some embodiments, the collagen binding peptides have homology to the amino acid sequence of a small leucine-rich proteoglycan or a platelet receptor sequence. In various embodiments the synthetic peptide comprises an amino acid sequence selected from the group consisting of RRANAALKAGELYKSILY (SEQ ID NO: 1), RRANAALKAGELYKCILY (SEQ ID NO: 2), SYIRIADTNIT (SEQ ID NO: 5), TKKTLRT (SEQ ID NO: 6), SQNPVQP (SEQ ID NO: 7), RLDGNEIKR (SEQ ID NO: 8), KELNVYT (SEQ ID NO: 9), KLWVLPK (SEQ ID NO: 10), CQDSETRTFY (SEQ ID NO: 11), AHEEISTTNEGVMGC (SEQ ID NO: 21), RLDGNEIKRGC (SEQ ID NO: 22), TKKTLRTGC (SEQ ID NO: 23), GLRSKSKKFRRPDIQYPDATDEDITSHMGC (SEQ ID NO: 24), SQNPVQPGC (SEQ ID NO: 25), SYIRIADTNITGC (SEQ ID NO: 26), SYIRIADTNIT (SEQ ID NO: 5), KELNLVYTGC (SEQ ID NO: 27), GSITTIDVPWNV (SEQ ID NO: 14), NGVFKYRPRYFLYKHAYFYPPLKRFPVQ (SEQ ID NO: 15), GELYKSILY (SEQ ID NO: 3), GELYKCILY (SEQ ID NO: 4), NGVFKYRPRYFLYKHAYFYPPLKRFPVQGC (SEQ ID NO: 28), GSITTIDVPWNVGC (SEQ ID NO: 29), RRANAALKAGELYKSILYGC (SEQ ID NO: 30), GELYKSILYGC (SEQ ID NO: 31), GCGGELYKSILY (SEQ ID NO: 32), WYRGRLC (SEQ ID NO: 19), WYRGRLGC (SEQ ID NO: 20), and an amino acid sequence with 80%, 85%, 90%, 95%, or 98% homology to any of these twenty eight amino acid sequences. The collagen binding peptide can also be any peptide of about 7 amino acids to about 40 amino acids, or 7 amino acids to 40 amino acids, selected from peptides that have collagen-binding activity and that are 80%, 85%, 90%, 95%, 98%, or 100% homologous with the collagen-binding domain(s) of the von Willebrand factor or a platelet collagen receptor as described in Chiang, et al. *J. Biol. Chem.* 277: 34896-34901 (2002), Huizinga, et al., *Structure* 5: 1147-1156 (1997), Romijn, et al., *J. Biol. Chem.* 278: 15035-15039 (2003), and Chiang, et al., *Cardio. & Haemato. Disorders-Drug Targets* 7: 71-75 (2007), each incorporated herein by reference.

In other illustrative embodiments, the collagen-binding peptide can be selected from the group consisting of RRANAALKAGELYKSILY (SEQ ID NO: 1), RRANAALKAGELYKCILY (SEQ ID NO: 2), SYIRIADTNIT (SEQ ID NO: 5), TKKTLRT (SEQ ID NO: 6), SQNPVQP (SEQ ID NO: 7), and RLDGNEIKR (SEQ ID NO: 8), can comprise the amino acid sequence GELYKXILY, wherein X is serine, cysteine, or threonine (SEQ ID NO: 16), can be RRANAALKAGELYKSILY (SEQ ID NO: 1), or can be RRANAALKAGELYKCILY (SEQ ID NO: 2).

Conservative and/or nonconservative amino acid substitutions are contemplated for all of the above-described peptides. Non-conservative substitutions are possible provided that these do not excessively affect the collagen binding activity of the peptide.

As is well-known in the art, a "conservative substitution" of an amino acid or a "conservative substitution variant" of a peptide refers to an amino acid substitution which maintains: 1) the secondary structure of the peptide; 2) the charge or hydrophobicity of the amino acid; and 3) the bulkiness of the side chain or any one or more of these characteristics. Illustratively, the well-known terminologies "hydrophilic residues" relate to serine or threonine. "Hydrophobic residues" refer to leucine, isoleucine, phenylalanine, valine or alanine, or the like. "Positively charged residues" relate to lysine, arginine, ornithine, or histidine. "Negatively charged residues" refer to aspartic acid or glutamic acid. Residues having "bulky side chains" refer to phenylalanine, tryptophan or tyrosine, or the like. A list of illustrative conservative amino acid substitutions is given in TABLE 1.

TABLE 1

| For Amino Acid | Replace With |
| --- | --- |
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

In various embodiments, the collagen binding peptide further comprises a cysteine added to the amino terminus or the carboxy terminus of the peptide. As used herein, the terms "amino terminus" or "carboxy terminus" refer to the first or last amino acid of the peptide.

In another embodiment, the added cysteine includes a spacer. In one embodiment, the spacer comprises one or more glycines. Illustratively, the spacer and cysteine may comprise a dipeptide of GC or CG, or a tripeptide of GCG. In one embodiment, wherein the cysteine is included with a spacer, the cysteine may then ultimately reside in the amino terminal region or carboxy terminal region. As used herein, the terms "amino terminal region" or "carboxy terminal region" refer to positions in the peptide that are 1, 2, 3, 4, or 5 positions from the amino terminus or carboxy terminus.

In one embodiment, the collagen binding peptide is synthesized according to solid phase peptide synthesis protocols that are well-known by persons of skill in the art. In one embodiment, a peptide precursor is synthesized on a solid support according to the well-known Fmoc protocol, cleaved from the support with trifluoroacetic acid and purified by chromatography according to methods known to persons skilled in the art.

In another embodiment the synthetic peptide is synthesized utilizing the methods of biotechnology that are well known to persons skilled in the art. In one embodiment a DNA sequence that encodes the amino acid sequence information for the desired peptide is ligated by recombinant DNA techniques known to persons skilled in the art into an expression plasmid (for example, a plasmid that incorporates an affinity tag for affinity purification of the peptide), the plasmid is transfected into a host organism for expression, and the peptide is then isolated from the host organism or the growth medium according to methods known by persons skilled in the art (e.g., by affinity purification). Recombinant DNA technology methods are described in Sambrook et al., "Molecular Cloning: A Laboratory Manual", 3rd Edition, Cold Spring Harbor Laboratory Press, (2001), incorporated herein by reference, and are well-known to the skilled artisan.

In any of the embodiments described herein, the nanoparticle coupled collagen binding peptides can be administered alone or in combination with suitable pharmaceutical carriers or diluents. Diluent or carrier ingredients used in the compositions containing collagen-binding peptides coupled to nanoparticles can be selected so that they do not diminish the desired effects of the nanoparticle coupled collagen binding peptides. Examples of suitable dosage forms include aqueous solutions of the collagen-binding peptide coupled nanoparticles, for example, a solution in isotonic saline, 5% glucose or other well-known pharmaceutically acceptable liquid carriers such as alcohols, glycols, esters and amides.

"Carrier" is used herein to describe any ingredient other than the active component(s) in a formulation. The choice of carrier will to a large extent depend on factors such as the particular mode of administration, the effect of the carrier on solubility and stability, and the nature of the dosage form. In one illustrative aspect, the carrier is a liquid carrier. In one illustrative aspect, the liquid carrier is a pharmaceutically acceptable carrier.

"Pharmaceutically acceptable" as used in this application, for example, with reference to salts and formulation components such as carriers, includes "veterinarily acceptable", and thus includes both human and animal applications independently. For example, a "patient" as referred to herein can be a human patient or a veterinary patient, such as a domesticated animal (e.g., a pet).

Pharmaceutically acceptable salts, and common methodologies for preparing pharmaceutically acceptable salts, are known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol. 66, No. 1, January 1977. *A preferred salt is the hydrochloride salt.*

The compositions described herein and their salts may be formulated as pharmaceutical compositions for systemic administration. Such pharmaceutical compositions and processes for making the same are known in the art for both humans and non-human mammals. See, e.g., REMINGTON: THE SCIENCE AND PRACTICE OF PHARMACY, (1995) A. Gennaro, et al., eds., 19$^{th}$ ed., Mack Publishing Co. Additional active ingredients may be included in the composition containing a collagen binding peptide coupled to a nanoparticle, or a salt thereof.

In one illustrative embodiment, pharmaceutical compositions for use with a composition comprising collagen binding peptides coupled to nanoparticles for parenteral administration comprise: a) a pharmaceutically active amount of the nanoparticle coupled collagen binding peptide; b) a pharmaceutically acceptable pH buffering agent to provide a pH in the range of about pH 4.5 to about pH 9; c) an ionic strength modifying agent in the concentration range of about 0 to about 300 millimolar; and d) water soluble viscosity modifying agent in the concentration range of about 0.25% to about 10% total formula weight or any combinations of a), b), c) and d) are provided.

In various illustrative embodiments, the pH buffering agents for use in the compositions and methods herein described are those agents known to the skilled artisan and include, for example, acetate, borate, carbonate, citrate, and phosphate buffers, as well as hydrochloric acid, sodium hydroxide, magnesium oxide, monopotassium phosphate, bicarbonate, ammonia, carbonic acid, hydrochloric acid, sodium citrate, citric acid, acetic acid, disodium hydrogen phosphate, borax, boric acid, sodium hydroxide, diethyl barbituric acid, and proteins, as well as various biological buffers, for example, TAPS, Bicine, Tris, Tricine, HEPES, TES, MOPS, PIPES, cacodylate, or MES.

In another illustrative embodiment, the ionic strength modulating agents include those agents known in the art, for example, glycerin, propylene glycol, mannitol, glucose, dextrose, sorbitol, sodium chloride, potassium chloride, and other electrolytes.

Useful viscosity modulating agents include but are not limited to, ionic and nonionic water soluble polymers; crosslinked acrylic acid polymers such as the "carbomer" family of polymers, e.g., carboxypolyalkylenes that may be obtained commercially under the Carbopol® trademark; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; gums such as tragacanth and xanthan gum; sodium alginate; gelatin, hyaluronic acid and salts thereof, chitosans, gellans or any combination thereof. Typically, non-acidic viscosity enhancing agents, such as a neutral or a basic agent are employed in order to facilitate achieving the desired pH of the formulation.

In one illustrative aspect, parenteral formulations may be suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art.

In one embodiment, the solubility of the nanoparticle coupled collagen binding polypeptides used in the preparation of a parenteral formulation may be increased by the use of appropriate formulation techniques, such as the incorporation of solubility-enhancing agents.

In various embodiments, formulations for parenteral administration may be formulated to be for immediate and/or modified release. Modified release formulations include delayed, sustained, pulsed, controlled, targeted and programmed release formulations. Thus, a nanoparticle coupled collagen binding peptide may be formulated as a solid, semisolid, or thixotropic liquid for administration as an implanted depot providing modified release of the active compound.

In other embodiments, nanoparticle coupled collagen binding peptides and compositions containing them can be administered topically. A variety of dose forms and bases can be applied to the topical preparations, such as an ointment, cream, gel, gel ointment, plaster (e.g. cataplasm, poultice), solution, powders, and the like. These preparations may be prepared by any conventional method with conventional pharmaceutically acceptable carriers or diluents as described below.

For example, vaseline, higher alcohols, beeswax, vegetable oils, polyethylene glycol, etc. can be used. In the preparation of a cream formulation, fats and oils, waxes, higher fatty acids, higher alcohols, fatty acid esters, purified water, emulsifying agents etc. can be used. In the preparation of gel formulations, conventional gelling materials such as polyacrylates (e.g. sodium polyacrylate), hydroxypropyl cellulose, hydroxypropyl methyl cellulose, polyvinyl alcohol, polyvinylpyrrolidone, purified water, lower alcohols, polyhydric alcohols, polyethylene glycol, and the like are used. In the preparation of a gel ointment preparation, an emulsifying agent (preferably nonionic surfactants), an oily substance (e.g. liquid paraffin, triglycerides, and the like), etc. are used in addition to the gelling materials as mentioned above. A plaster such as cataplasm or poultice can be prepared by spreading a gel preparation as mentioned above onto a support (e.g. fabrics, non-woven fabrics). In addition to the above-mentioned ingredients, paraffins, squalane, lanolin, cholesterol esters, higher fatty acid esters, and the like may optionally be used. Moreover, antioxidants such as BHA, BHT, propyl gallate, pyrogallol, tocopherol, etc. may also be incorporated. In addition to the above-mentioned preparations and components, there may optionally be used any other conventional formulations for incorporation with any other additives.

In various embodiments, the dosage of the nanoparticle coupled collagen binding peptides can vary significantly depending on the patient condition, the disease state being treated (e.g., arthritis) or the imaging technique being used, the route of administration and tissue distribution, and the possibility of co-usage of other therapeutic treatments or imaging agents. The effective amount to be administered to a patient is based on body surface area, patient weight or mass, and physician assessment of patient condition.

Suitable dosages of the nanoparticle coupled collagen binding peptides can be determined by standard methods, for example by establishing dose-response curves in laboratory animal models or in humans in clinical trials. Illustratively, suitable dosages of nanoparticle coupled collagen binding peptides (administered in a single bolus or over time) include from about 1 pg/kg to about 10 µg/kg, from about 1 pg/kg to about 1 µg/kg, from about 100 pg/kg to about 500 ng/kg, from about 1 pg/kg to about 1 ng/kg, from about 1 pg/kg to about 500 pg/kg, from about 100 pg/kg to about 500 ng/kg, from about 100 pg/kg to about 100 ng/kg, from about 1 ng/kg to about 10 mg/kg, from about 1 ng/kg to 1 mg/kg, from about 1 ng/kg to about 1 µg/kg, from about 1 ng/kg to about 500 ng/kg, from about 100 ng/kg to about 500 µg/kg, from about 100 ng/kg to about 100 µg/kg, from about 1 µg/kg to about 500 µg/kg, or from about 1 µg/kg to about 100 µg/kg. In each of these embodiments, dose/kg refers to the dose per kilogram of a patient's or animal's mass or body weight.

In another illustrative aspect, any of the above described composition embodiments can be used in a method for imaging a collagenous matrix. For example, in one embodiment, a composition for use in imaging a collagenous matrix is provided. The composition comprises at least one collagen binding polypeptide coupled to a nanoparticle, wherein the polypeptide contains from 7 amino acids to 40 amino acids and wherein the polypeptide does not form a triple helix. In another illustrative embodiment, a method for imaging a collagenous matrix is provided. The method comprises the steps of contacting a collagenous matrix with a composition comprising at least one collagen binding polypeptide coupled to a nanoparticle, wherein the polypeptide contains from 7 amino acids to 40 amino acids and wherein the polypeptide does not form a triple helix, and imaging the collagenous matrix.

The collagen-binding gold nanoparticles described herein, for example, are useful for a variety of biomedical imaging techniques including SEM, TEM, confocal microscopy, MRI, and photoacoustic imaging. Further, radiopaque nanoparticles that are coupled with collagen binding proteins can be used in radiologic imaging such as CT scan or X-ray. The imaging methods in which the collagen-binding peptides coupled to nanoparticles are useful include both in vitro imaging methods and imaging methods applicable to a human or a veterinary patient. For example, any tissue can be imaged to which a collagen binding polypeptide coupled to a nanoparticle can be targeted.

Exemplary of tissues containing collagen that may be imaged in accordance with the methods and compositions described herein include submucosa tissues (e.g., intestinal, urinary bladder tissue, and stomach tissue), pericardial tissue, skin tissue, bone, cartilage, tendon, other connective tissues of any animal, and any other collagen containing tissues of an animal.

In another embodiment, the compositions described herein can be used for targeted drug delivery (e.g., to target drugs to tissues using the collagen binding polypeptide as the targeting agent). For example, the compositions can be used for targeted delivery of drugs to specific tissues, and further to increase solubility of drugs under physiological conditions. Solubility limits have prevented the use of numerous effective drugs. However, solubility problems can be overcome by the use of nanoparticles, in which the insoluble compound is encapsulated. In other embodiments, the nanoparticles can be used to control drug release using engineered nanoparticles with specifically designed geometries and degradation profiles, making possible the release of effective drug doses over long periods of time.

Peptides can be coupled to nanoparticles by employing a variety of chemistries, for example, such as those described in Bioconjugate Techniques (Greg T. Hermanson, Academic Press; 2 edition (May 2, 2008)), incorporated herein by reference. Illustratively, a collagen binding sequence, for example, RRANAALKAGELYKSILY (SEQ ID NO: 1) may be modified such that it contains a glycine spacer followed by a cysteine at the carboxy terminus yielding the sequence RRANAALKAGELYKSILYGC (SEQ ID NO: 30).

The sulfhydryl group contained in the cysteine may then be used to couple the peptide to gold on the gold nanoparticle. PEG-SH is first coupled to the gold nanoparticles through its sulfhydryl group, then excess PEG-SH is removed by centrifugation and reconstituting the particles in PBS buffer. The modified collagen-binding peptide is then incubated with PEG functionalized gold nanoparticles in excess, such that the peptide couples to the gold.

Other chemistry techniques may be used for coupling peptides to nanoparticles depending on the peptide sequence. For example, if the collagen-binding peptide sequence contains an internal cysteine which cannot be modified, it may be possible to use an amine group for coupling. Crosslinking molecules may be used for such coupling. For example, a heterobifunctional crosslinker commercially available from Thermo Scientific that couples amines to sulfhydryl groups may be used.

Example 1

Nanoparticle Functionalization

Gold nanoparticles (NP) of 13 nm size were prepared as previously described and stabilized with citrate until further functionalization (Jeong et al. (2008) *Langmuir* (16):8794-8800; Storhoff et al. (1998) *JACS* 120(9):1959-1964). Peptide (SILY$_{biotin}$ (SEQ ID NO: 33)) was purchased from Genscript (Piscataway, N.J.). Monofunctional PEG-SH (1 kDa, 2 kDa, or 5 kDa) was purchased from Layasan Bio (Arab, Ala.). Streptavidin-HRP and color evolving solutions were purchased from R&D Systems (Minneapolis, Minn.). All other reagents were purchased from VWR (Radnor, Pa.).

Gold nanoparticles were functionalized following a previously described method (Liu et al. (2007) *Analytical Chem.* 79(6):2221-2229). Monofunctional PEG-SH was dissolved in 1×PBS pH 7.4 to a final concentration of 0.01 mg/mL. PEG-SH was added to 1 mL of 13 nm NP in citrate to a final molar ratio of 2,500:1 (PEG:NP) and allowed to react for 1 hour at room temperature. PEG functionalized GNP (PEG-NP) was then pelleted by centrifuging at 15,000 RPM for 15 minutes. The supernatant was removed and particles were reconstituted in 1×PBS pH 7.4. The process was repeated 2 more times to remove excess PEG.

Biotin labeled peptide (SILY$_{biotin}$ (SEQ ID NO: 33)) was dissolved in ultrapure water to a final concentration of 2 mg/mL, and was added to purified PEG-NP at a molar ratio of 1,000:1 (SILY$_{biotin}$:PEG-NP ('SILY$_{biotin}$' disclosed as SEQ ID NO: 33)). Peptide coupling to the NP was reacted overnight at room temperature. Excess peptide was removed by centrifugation as described for PEG purification and was repeated 3 times. The final product PEG-NP-SILY ('SILY' disclosed as SEQ ID NO: 17) was then brought up to a stock concentration of approximately 10 nM and was used within 2 days of synthesis.

Example 2

Collagen-Binding of Nanoparticles

Fibrillar collagen (Chronolog, Havertown, Pa.) was diluted in isotonic glucose to 0.1 mg/mL and was coated onto 96-well plates (Greiner) overnight at 4 C. Control wells were coated with 1% BSA in 1×PBS pH 7.4 at room temperature for 1 hour. All wells were then rinsed with 1×PBS pH 7.4 to remove unbound collagen or BSA. PEG-NP-SILY ('SILY' disclosed as SEQ ID NO: 17) was then incubated on the surfaces at varying concentrations and allowed to bind for 30 min at room temperature. Wells were then rinsed with 1×PBS 3 times to remove unbound PEG-NP-SILY ('SILY' disclosed as SEQ ID NO: 17). Bound PEG-NP-SILY ('SILY' disclosed as SEQ ID NO: 17) was then detected by probing for biotin using Streptavidin-HRP following manufacturers protocol.

Stability of PEG-NP-SILY ('SILY' Disclosed as SEQ ID NO: 17)

Gold nanoparticles will aggregate in solution unless stabilized, such as in citrate buffer. In 1×PBS gold nanoparticles immediately precipitate, and conjugating the SILY peptide (SEQ ID NO: 17) to nanoparticles also results in aggregation in PBS. PEG is therefore used to stabilize the nanoparticles. Sequential coupling of PEG following by SILY (SEQ ID NO: 17) was previously shown to be an effective method of functionalizing the NP with peptide. Here, the same method was employed to couple SILY (SEQ ID NO: 17).

Binding to Type I Collagen

The molecular weight of PEG plays a significant role in the function of PEG-NP-SILY ('SILY' disclosed as SEQ ID NO: 17) as shown in FIG. 1. While PEG-1kDa allows for binding to collagen, there is significant nonspecific binding to the BSA surface and was thus not used (data not shown). Conversely, PEG-2 kDa and PEG-5 kDa result in specific binding of the functionalized NP to collagen with minimal binding to the BSA surface. Increased binding was observed with PEG-2 kDa compared with PEG-5 kDa. This result is due to the size of the peptide, in which SILY (SEQ ID NO: 17) is 2197 Da, and is thus excluded to some degree with 5 kDa PEG. The optimum molecular weight of PEG is thus from 2 kDa to 5 kDa, and could vary depending on the peptide sequence.

Figure 2:
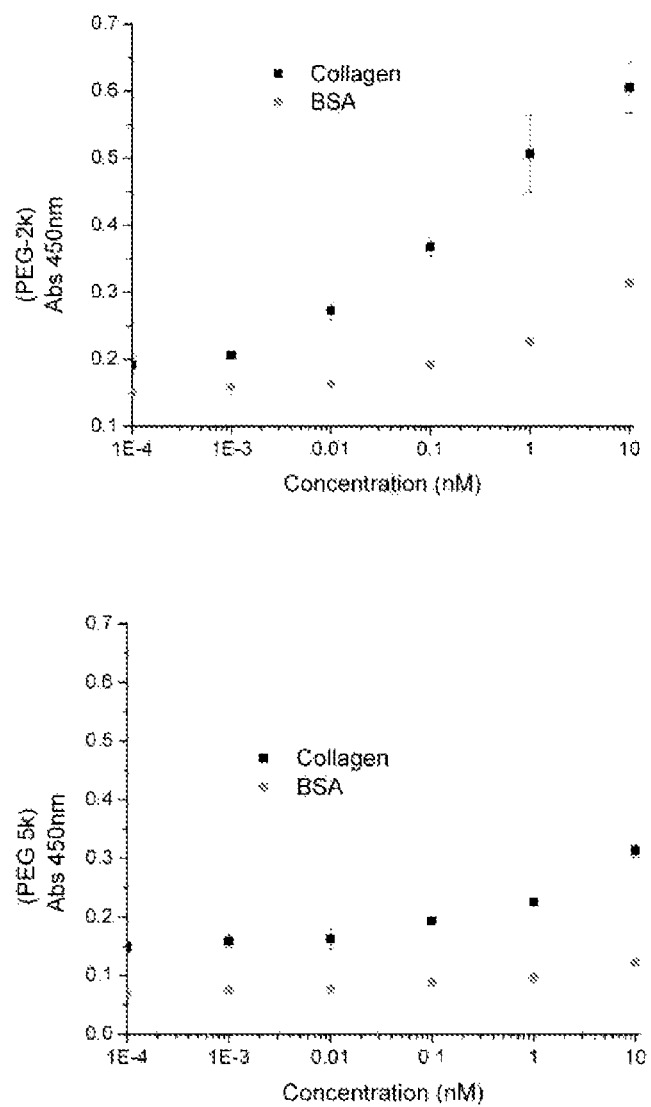
FIG. 2. Binding of functionalized nanoparticles to collagen. NP functionalized with 2 kDa PEG showed increased binding to collagen compared to 5 kDa PEG. This is due to the length of the peptide SILY (SEQ ID NO: 17), which is 2197 Da and is masked in part by the higher molecular weight PEG. Minimal nonspecific binding to BSA was observed in both functionalized nanoparticles.

NP functionalized with 2 kDa PEG showed increased binding to collagen compared to 5 kDa PEG. This is due to the length of the peptide SILY (SEQ ID NO: 17), which is 2197 Da and is masked in part by the higher molecular weight PEG. Minimal nonspecific binding to BSA was observed in both functionalized nanoparticles (FIG. 2).

Example 3

Visualization of SILY ('SILY' Disclosed as SEQ ID NO: 17) Functionalized Gold Nanoparticles on Rat Tail Tendon Collagen Gold nanoparticles of 60 nm diameter were purchased from Cytodiagnostics (Burlington, ON). Particles were functionalized with PEG-thiol followed by free SILY$_{biotin}$ (SEQ ID NO: 33) peptide yielding GNP-SILY ('SILY' disclosed as SEQ ID NO: 17). Rat tail tendons were harvested from Sprague-Dawley rats and rinsed in 1×PBS immediately prior to testing. Plates (96-well) were coated with 1% BSA to prevent nonspecific binding, and rinsed 3× to remove unbound BSA. Tendons were then incubated for 15 min at room temperature in 100 µL/well of approximately 0.01 nM GNP-SILY ('SILY' disclosed as SEQ ID NO: 17) in 1×PBS pH 7.4 or in control nanoparticles which were functionalized with PEG only (GNP-PEG). Tendons were then rinsed in 3× in 200 µL 1×PBS for 5 minutes per rinse to wash of unbound nanoparticles. Samples were fixed in 2.5% glutaraldehyde in 1×PBS pH 7.4 at 4° C. for 2 hours followed by rinsing and dehydration in graded ethanol up to 100% and air dried.

Figure 3:
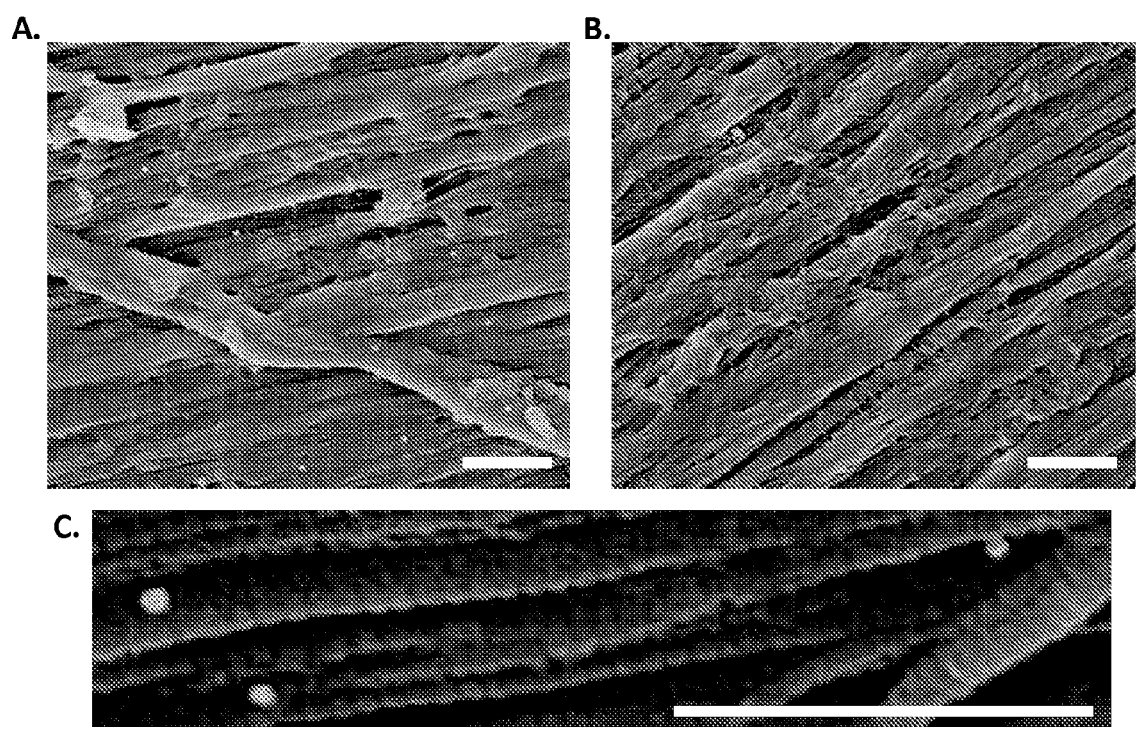
FIG. 3. Nanoparticles localized on rat tail tendon. Tendons were incubated with gold nanoparticles functionalized with either SILY peptide (SEQ ID NO: 17) or PEG control. In A., GNP-SILY ('SILY' disclosed as SEQ ID NO: 17) 60 nm spheres can be seen on the surface of collagen fibers in contrast to B. which was treated with GNP-PEG control spheres. A closer image in C. shows GNP-SILY ('SILY' disclosed as SEQ ID NO: 17) binding along D-banded collagen fibers where it appears to bind in the overlap zone close to the following gap region. In all images, scale bar=1 µm.

Tendons were platinum sputter coated and examined by SEM. Representative images shown in FIG. 3 demonstrate specific binding of GNP-SILY ('SILY' disclosed as SEQ ID NO: 17) to collagen in tendons as noted by the 60 nm spheres. In contrast, control tendon incubated with GNP-PEG did not contain any nanoparticles. The number of particles bound to the tendon was rather sparse and is most likely due to the very low concentration of nanoparticles (0.01 nM). To increase particle binding, nanoparticles may be further concentrated prior to incubating tendons.

Example 4

Core+Shell Nanoparticle Synthesis

Figure 4:
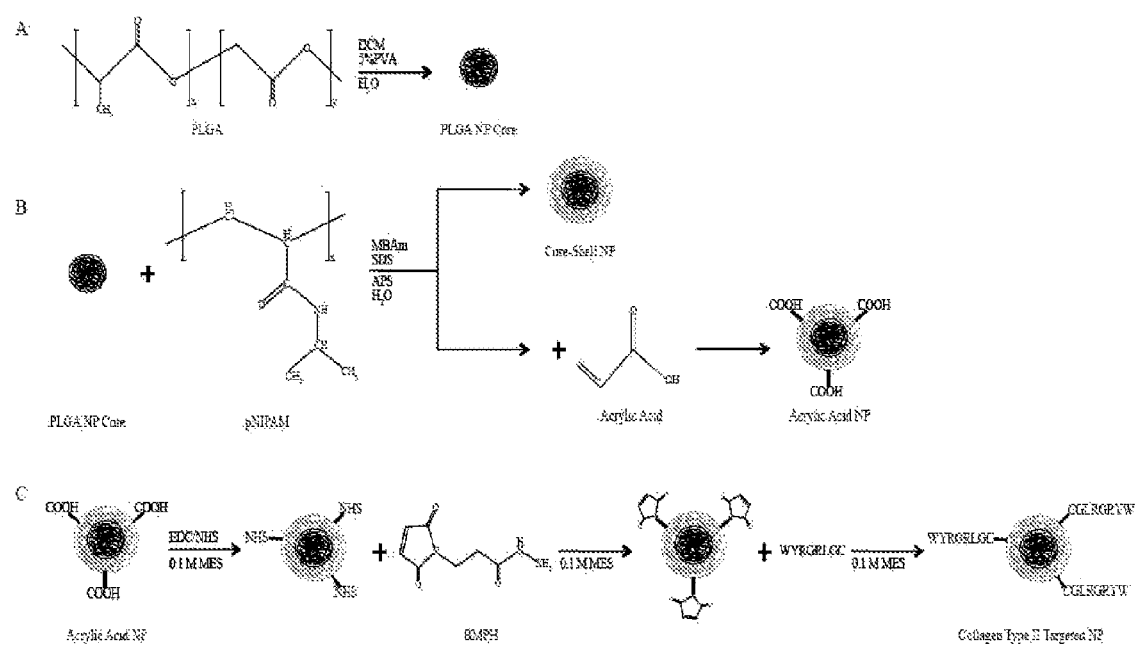
FIG. 4. Schematic of the synthesis of PLGA core+pNIPAM shell nanoparticles (A and B) and the subsequent chemistry (C) used to target the nanoparticles to collagen type II.

Synthesis of the core+shell nanoparticles occurred in two steps: synthesis of the Poly(lactic-co-glycolic acid) (PLGA) cores followed by the addition of the poly(N-isopropylacrylamide) (pNIPAM) shell (FIG. 4). PLGA cores were synthesized using a single emulsion technique. Briefly, 5 g of poly (dl-lactide/glycolide) 50:50 (PLGA; Polysciences Inc.) were dissolved in 5 mL of dichloromethane (DCM; Sigma-Aldrich), added to 20 mL of 5% polyvinyl alcohol (PVA; Alfa Aesar), and homogenized for 30 s using a probe sonicator (Branson Sonifier 450) to generate a single emulsion. The emulsion was added to 100 mL of rapidly stirred distilled water and left overnight to allow for full evaporation of the DCM. The PLGA nanoparticles were further purified via centrifugation washes with distilled water. Any clumps of PLGA nanoparticles that remained after centrifugation were disrupted using brief sonication.

The PLGA cores were encapsulated in pNIPAM shells using aqueous free radical precipitation polymerization under a nitrogen atmosphere. Briefly, 0.27 g N-isopropylacrylamide [2.385 mmol] (Polysciences Inc.), 0.021 g N-N'-methylene bisacrylamide [0.136 mmol] (Fluka), 0.012 g sodium dodecyl sulfate [0.042 mmol] (Sigma Aldrich), and 0.015 g ammonium persulfate [0.066 mmol] (Sigma Aldrich) were dissolved in 30 mL of distilled water and purged of oxygen by nitrogen bubbling. For nanoparticle targeting, either 1.670 [0.024 mmol or 1 mol %] or 8.35 µl [0.121 mmol or 5 mol %] of acrylic acid (AAc; Alfa Aesar) were included. 20 mL of the PLGA nanoparticle cores were added to a 250 mL three-neck round bottom flask and equilibrated to 70° C. for 20 minutes under nitrogen with stirring. 10 mL of the shell solution was added to the 70° C. equilibrated PLGA nanoparticle cores and allowed to polymerize. Additional 5 mL aliquots of shell solution were added 30, 50, 70, and 90 minutes after the initial polymerization. Polymerization continued for 6 hours after the final addition of shell solution. Purification was achieved through dialysis of the PLGA core+pNIPAM shell nanoparticles against distilled water for 7 days in 15,000 MWCO dialysis tubing (Spectrum Laboratories, Inc.). Centrifugation washes were performed in order to further isolate the core+shell nanoparticles. Any clumps of core+shell nanoparticles post centrifugation were dispersed using brief sonication. A portion of the samples were lyophilized and then rehydrated in distilled water.

Example 5

Transmission Electron Microscopy (Tem) Characterization

Images were taken of the pre- and post-lyophilized nanoparticle samples by staining them with 2% uranyl acetate. The stained nanoparticles were placed on a glow-discharged 400 mesh coated with formvar+carbon film, and placed in a Philips CM-100 TEM where images were captured on Kodak SO-163 electron image film.

Figure 5:
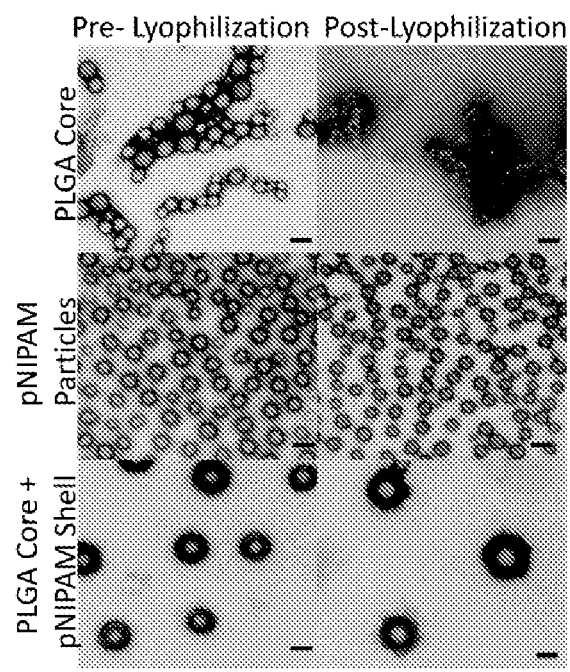
FIG. 5. Transmission electron microscope images of the various nanoparticles both pre- and post-lyophilization. Scale bars=250 nm.

Lyophilization is an effective way to prevent the release of therapeutics loaded into PLGA nanoparticles during long-term storage. TEM imaging was used to visually confirm that well-defined spherical PLGA and PLGA core+pNIPAM shell nanoparticles were successfully synthesized pre-lyophilization (FIG. 5). TEM imaging showed that post lyophilization the PLGA nanoparticles form aggregates (FIG. 5). This aggregation resulted in an inability to measure diameter and ζ-potential of post-lyophilized PLGA nanoparticles. In contrast, encapsulation of PLGA nanoparticles with pNIPAM shells prevented aggregation of the PLGA nanoparticles following lyophilization, further confirming that the pNIPAM shell fully encapsulated the PLGA core. Furthermore, lyophilization of the core+shell nanoparticles did not affect the size or ζ-potential of the particles at 25° C. or 37° C. (Table 1).

Example 6

Nanoparticle Sizing and Zeta Potential

Measurements were taken with a Malvern Zetasizer Nano Z590. Pre- and post-lyophilized nanoparticles were suspended in distilled water and analyzed for particle size in polystyrene cuvettes at 25° C. and 37° C. Temperature sweeps were performed by varying temperature from 20° C. to 50° C. to 20° C. in 1° increments with measurement of particle size with each change in degree. Disposable Malvern ζ-potential cuvettes were used to acquire ζ-potential measurements at 25° C. and 37° C. After making any change in temperature, nanoparticle samples were allowed to equilibrate for five minutes before any sizing or zeta measurements were made.

Verification of successful encapsulation of the PLGA cores with the pNIPAM shells was initially achieved using dynamic light scattering to measure the size of the nanoparticles before and after the addition of the shell to determine the change in nanoparticle diameter. The diameter of the core+shell nanoparticles (Table 1) increased post addition of the pNIPAM shell suggesting successful encapsulation. pNIPAM shell thickness ranged from ~100 nm to ~200 nm at 25° C., with an increase in shell thickness corresponding to an increase in the mole percent of acrylic acid incorporated into the pNIPAM.

Additional verification of the successful encapsulation of the pNIPAM shell was provided by confirming a phase transition when the temperature was raised above its lower critical solution temperature (LCST). All core+shell nanoparticles had reduced diameters at 37° C. compared to 25° C. (Table 1).

To assess colloidal stability of the core+shell nanoparticles above and below the phase transition temperature, the ζ-potentials were measured. Typically, nanoparticle ζ-potentials above 30 mV or below −30 mV are considered stable.

TABLE 1

Characterization of Various Nanoparticle Samples.

| Sample Name | Lyophilization? | T (° C.) | Particle Diameter (nm) | Zeta Potential (mV)[a] | Shell Thickness (nm)[b] |
|---|---|---|---|---|---|
| PLGA Core | No | 25 | 392.3 ± 13.9 | −32.1 ± 2.0 | NA |
| | | 37 | 377.2 ± 20.2 | −22.5 ± 3.4 | |
| PLGA Core + pNIPAM Shell 0% AAc | No | 25 | 605.3 ± 10.8 | −28.3 ± 4.4 | 106.5 ± 5.4 |
| | | 37 | 403.8 ± 7.1 | −25.0 ± 2.5 | 13.3 ± 3.6 |
| | Yes | 25 | 610.2 ± 14.2 | −32.1 ± 0.9 | 109.0 ± 7.1 |
| | | 37 | 414.5 ± 7.9 | −24.3 ± 1.8 | 18.6 ± 3.9 |
| PLGA Core + pNIPAM Shell 1% AAc | No | 25 | 659.1 ± 6.7 | −28.0 ± 6.0 | 133.4 ± 3.4 |
| | | 37 | 428.0 ± 9.5 | −22.7 ± 2.7 | 25.4 ± 4.7 |
| | Yes | 25 | 681.7 ± 20.9 | −30.8 ± 5.1 | 144.7 ± 10.4 |
| | | 37 | 447.0 ± 13.5 | −20.5 ± 0.7 | 34.9 ± 6.8 |
| PLGA Core + pNIPAM Shell 5% AAc | No | 25 | 748.5 ± 17.1 | −34.9 ± 2.5 | 178.1 ± 8.5 |
| | | 37 | 534.1 ± 14.8 | −25.1 ± 3.1 | 78.4 ± 7.4 |
| | Yes | 25 | 818.3 ± 3.9 | −34.6 ± 0.2 | 213.0 ± 2.0 |
| | | 37 | 575.9 ± 16.6 | −25.2 ± 2.1 | 99.4 ± 8.3 |

[a]pH of all samples was between 5 and 6.
[b]Determined by subtracting corresponding core from core + shell sample and dividing by 2.

Figure 6:
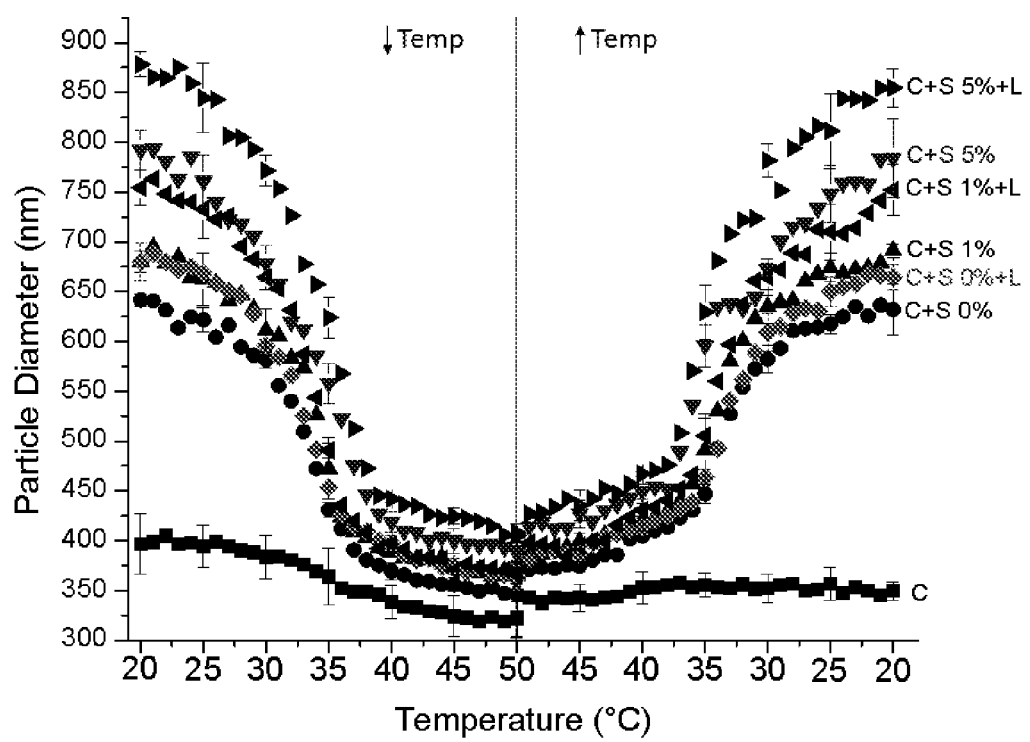
FIG. 6. Temperature sweeps of the various nanoparticles. Data is represented as mean±standard deviation (n=3). C=PLGA core only; C+S #%=PLGA core+pNIPAM shell+mol % acrylic acid; L=Lyophilized.

To further assess the response of the core+shell nanoparticles to temperature-based environmental stimuli, dynamic light scattering was used to measure the diameter of the core+shell nanoparticles as they were exposed to a dynamic range of temperatures from 20° C. to 50° C. to 20° C. The core+shell nanoparticles readily responded within this temperature range with all core+shell nanoparticle types decreasing in diameter as the temperature was raised above the LCST (FIG. 6). This response was reversible as the nanoparticles returned to their original diameter when the temperature was lowered back below the LCST. Additionally, the LCST of the pNIPAM shell was tuned by modifying the amount of acrylic acid that was incorporated as a co-monomer. As more acrylic acid was incorporated, the LCST of pNIPAM increased (FIG. 6). The core+shell nanoparticles with 0 mol % acrylic acid exhibited an LCST at ~31-32° C., while the 1 mol % acrylic acid had an LCST at ~33-34° C., and the core+shell nanoparticles with 5% acrylic acid had an LCST at ~35° C. (FIG. 6).

Example 7

Peptide Synthesis and Purification

The collagen type II binding peptide single amino acid sequence consisting of WYRGRLGC (SEQ ID NO: 20) was used. The peptide was synthesized at a 0.4 mmol scale on Knorr-amide resin (Synbiosci Corp.) using standard FMOC (9-fluorenylmethyloxycarbonyl) chemistry. Two different chemistries were used to couple each amino acid (Synbiosci Corp). The first coupling reagents consisted of N-hydroxybenzotriazole (HOBt; Synbiosci) and N,N' diisopropylcarbodiimide (DIC; Sigma-Aldrich) and the second coupling reagents were 0-Benzotriazole-N,N,N',N'-tetramethyl-uronium-hexafluoro-phosphate (HBTU; Synbiosci) and lutidine (Sigma-Aldrich). Following synthesis, the peptide was cleaved from the resin with 95% trifluoroacetic acid (Sigma-Aldrich), 2.5% water, 1.25% triisopropylsilane (Sigma-Aldrich), and 1.25% ethanedithiol (Sigma-Aldrich), precipitated in cold ether, and recovered by centrifugation. The peptide was purified with an acetonitrile gradient on an AKTA Explorer FPLC (GE Healthcare) equipped with a 22/250 C18 reversed phase column (Grace Davidson). Molecular weight was confirmed by time of flight MALDI mass spectrometry using a 4800 Plus MALDI TOF/TOF Analyzer (Applied Biosystems). Theoretical molecular weight of WYRGRLC (SEQ ID NO: 19) was calculated to be 1009.1 while the actual molecular weight was found to be 1009.58. A biotinylated version of the peptide (biotin-WYRGRLC (SEQ ID NO: 34)) was purchased from Genscript and its theoretical molecular weight was calculated to be 1179.42 while its actual molecular weight was found to be 1179.8.

Example 8

Modifying Core+Shell Nanoparticle with Targeting Moiety

Nanoparticle targeting was achieved through the addition of a collagen binding peptide to the AAc groups on our core+shell nanoparticles using a heterobifunctional crosslinker. Briefly, 0.4 mg of 1-ethyl-3-[3-dimethylaminopropyl]carbodiimide hydrochloride (EDC; Thermo-Scientific) and 1.1 mg of N-hydroxylsulfosuccinimide (Sulfo-NHS; Thermo-Scientific) were added to 1 mg of core+shell nanoparticles for 15 minutes in activation buffer (0.1M 2-(N-morpholino)ethanesulfonic acid (MES; Amresco) pH 6.0). Excess EDC and sulfo-NHS was removed by a centrifuge wash. The heterobifunctional crosslinker, N-[β-maleimidopropionic acid] hydrazide (BMPH; Thermo-Scientific) was added to the activated nanoparticles (0.1 mg for 1 mol % AAc nanoparticles or 0.3 mg for 5 mol % AAc nanoparticles) for 2 hours in coupling buffer (0.1M MES, pH 7.2). Excess BMPH was removed using gel filtration chromatography (GFC) through an ÄKTA Purifier FPLC (GE Healthcare) with Bio-Scale Mini Bio-Gel columns packed with polyacrylamide beads (Bio-Rad Laboratories). The collagen binding peptide (15% biotinylated) was added to the nanoparticles for 2 hours in coupling buffer. Excess peptide was removed via gel filtration chromatography. Confirmation of peptide addition was performed using a flouraldehyde assay (Pierce), which reacts with free amines and a streptavidin color development assay which confirmed the presence of the biotinylated peptide on the nanoparticle surface (data not shown).

The acrylic acid allowed the addition of a heterobifunctional crosslinker, e.g., BMPH, using EDC/NHS chemistry. The thiol based cysteine in the collagen binding peptide was reacted with a maleimide based BMPH. This chemistry can be applied to attach other targeting moieties that contain a free thiol functional group.

Example 9

Collagen Binding Assay

Modified nanoparticles were tested for their ability to bind to collagen. A 96-well plate (Greiner) was coated with collagen type II from chicken sternum (Sigma) in 0.25% acetic acid at a concentration of 0.5 mg/ml overnight. Following three washes, the plate was blocked with 1% bovine serum albumin (BSA; SeraCare Life Systems) for 1 hour. After three more washes, the collagen type II binding peptide modified core+shell nanoparticles and unmodified controls were incubated in the collagen type II coated plate for 1 hour. Following three more washes, streptavidin (R&D Systems) was diluted 200× in 1% BSA and incubated for 20 minutes in the plate. After more washing to remove unbound streptavidin, a color solution (R&D Systems) was added for 20 minutes. Sulfuric acid (Mallinckrodt Chemicals) was used to stop the reaction and absorbance was read at 450 nm with a correction at 540 nm.

Figure 9:
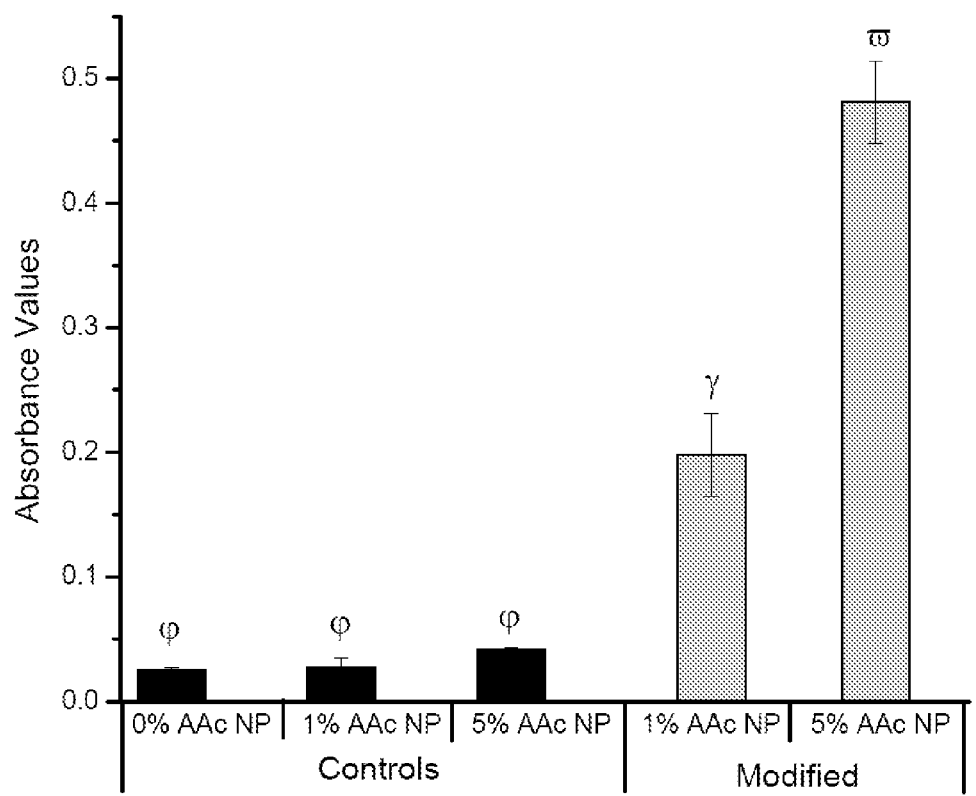
FIG. 9. Collagen Type II binding assay for C+S nanoparticles. Different Greek letters represent statistical significance ($p<0.05$; One-way ANOVA+Tukey Post-hoc test). Data presented as mean±standard deviation (n=4).

To assess whether incorporation of a collagen binding peptide would allow the core+shell nanoparticles to bind to collagen, a streptavidin ELISA was used. The results from the assay indicate that core+shell nanoparticles modified with collagen type II binding peptide bound collagen type II as compared to unmodified core+shell nanoparticle controls (FIG. 9; p<0.05, One-way ANOVA+Tukey post hoc test). Furthermore, the number of collagen type II binding peptide modified core+shell nanoparticles able to bind to collagen type II was directly related to the concentration of acrylic acid that was incorporated into the pNIPAM shell.

Example 10

Cell Culture and Nanoparticle Biocompatibility

Immortalized human monocytes (THP-1, ATCC) were grown in RPMI 1640 with L-glutamine (Mediatech Inc) supplemented with 0.05 mM mercaptoethanol (Sigma-Aldrich), 10 mM HEPES (Mediatech Inc), 1 mM sodium pyruvate (Mediatech Inc), 10% fetal bovine serum (Hyclone), and 1% penicillin/streptomycin (Mediatech Inc). Cells were used between passage number 4 and 12 for all assays and maintained at 37° C. with 5% CO2.

The biocompatibility of the nanoparticles was assessed by measuring toxicity and inflammation in THP-1 cells. Cells were seeded at a density of 250,000 cells/ml in 96-well plates (Corning) and treated with 10 ng/ml phorbol 12-myristate 13-acetate (PMA, Sigma-Aldrich) for 48 hours to induce differentiation, which was confirmed by the monocytes becoming adherent. Following a change of media, cells were treated with various concentrations of core+shell nanoparticles. Control samples received PBS (negative control) or 50 ng/ml lipopolysaccharide (LPS, Sigma-Aldrich) (positive control). After 24 hours, the media was collected for cytokine analysis and an MTT-based assay was performed to determine cell toxicity using the Aqueous One Proliferation Kit (Promega) according to manufacturer's instructions. Briefly, 20 μl of reagent was added directly to 100 μl of cells and media. After two hours of incubation in the cell culture incubator, the absorbance was read at 490 nm with a correction at 650 nm.

Figure 7:
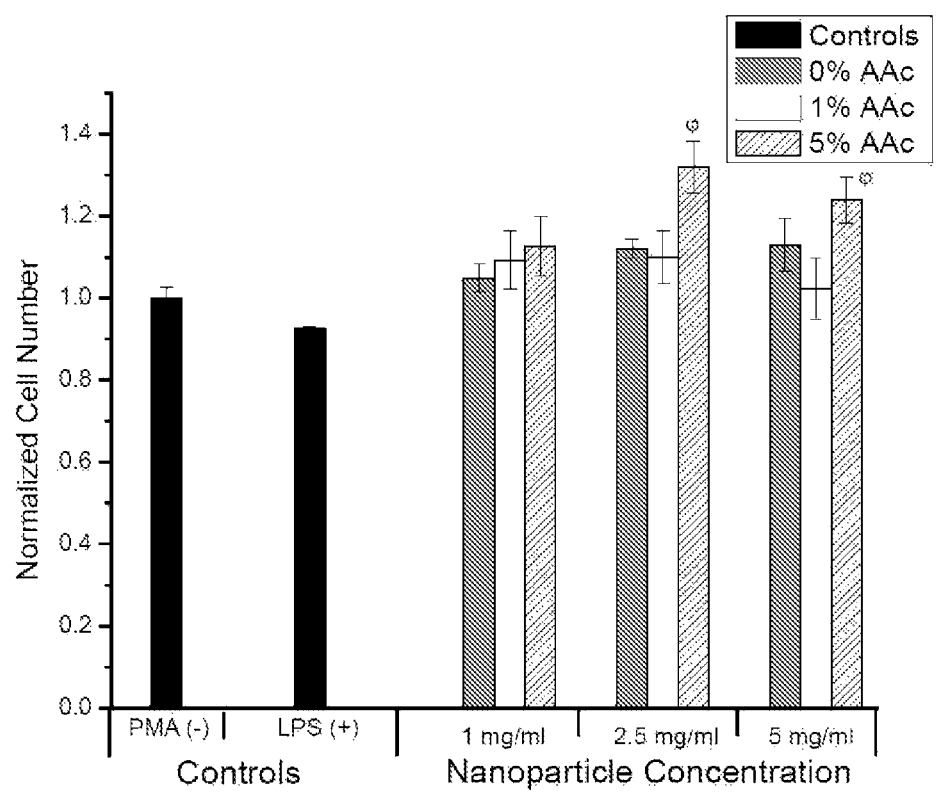
FIG. 7. Toxicity of the core+shell nanoparticles in human monocytes. φ represents $p<0.05$ compared to all other treatments (One-way ANOVA+Tukey post-hoc test). Data is presented as mean±standard deviation (n=4).
Figure 8:
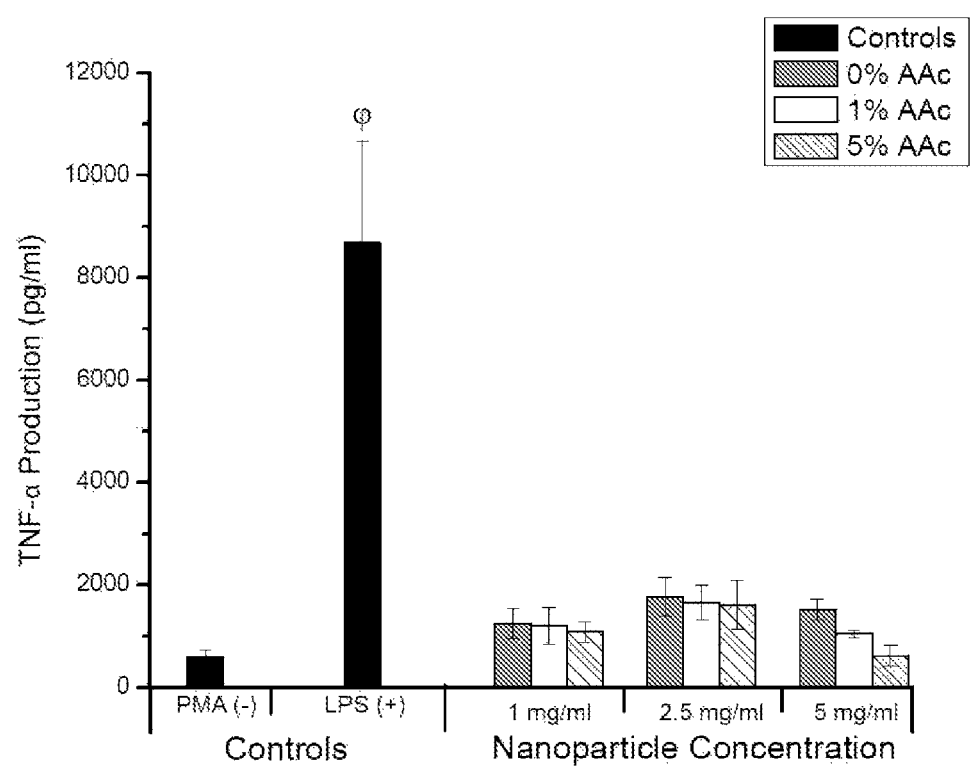
FIG. 8. TNF-α production by human monocytes treated with core+shell nanoparticles. φ represents statistical significance from all other data points ($p<0.05$, One-way ANOVA+Tukey Post-hoc test). Data presented as mean±standard deviation (n=4).

The biocompatibility of the core+shell nanoparticles was assessed by evaluating the toxicity and inflammatory response in an immortalized human monocyte cell line, i.e., THP-1 cells. Monocytes have a significant role in the perpetuation of osteo- and rheumatoid arthritis. The core+shell nanoparticles were not toxic at any of the concentrations tested as no significant reduction in THP1 proliferation was observed (FIG. 7). However, the core+shell nanoparticles with 5 mol % acrylic acid induced a significant increase in proliferation of the THP-1 cells at concentrations of 2.5 and 5 mg/mL compared to all other treatments (One-way ANOVA p<0.05; Tukey post-hoc test). The ability of the core+shell nanoparticles to elicit an inflammatory response was determined by measuring TNF-α production by THP-1 cells using an ELISA. Similar to the PBS control, the core+shell nanoparticles did not elicit TNF-α production (FIG. 8; p>0.05 One-way ANOVA). The positive control, THP-1 cells treated with lipopolysacharide, did induce TNF-α production as expected.

Example 11

Cytokine Analysis

The ability of the particles to cause an inflammatory response was determined by running conditioned cell media on a TNF-α ELISA (PeproTech) according to manufacturer instructions. Briefly, Nunc MaxiSorp 96-well plates were coated with capture antibody overnight. After blocking for one hour with 1% bovine serum albumin (Sera Lifesciences) in PBS, samples and standards were incubated for two hours with gentle rotation. Following incubation with a detection antibody and an avidin-horse radish peroxidase conjugate, the samples were developed with the addition of 2,2'-azino-bis(3-ethylbenzthiazoline-6-sulphonic acid) (ABTS) liquid substrate (Sigma-Aldrich) and monitored at 405 nm with a correction at 650 nm.

Example 12

Statistical Analysis

Data was analyzed for differences using a single factor ANOVA with a Tukey post-hoc test. An $\alpha=0.05$ was used for all analyses. Graphs are depicted as mean±standard deviation.

What is claimed is:

1. A composition comprising at least one collagen binding polypeptide covalently bound to a polymeric nanoparticle, wherein the polypeptide contains from 7 amino acids to 40 amino acids and wherein the polypeptide does not form a triple helix.

2. The composition of claim 1 wherein the nanoparticle further comprises a stabilizer.

3. The composition of claim 2 wherein the stabilizer is selected from the group consisting of a polyethylene glycol (PEG), a dextran, a peptide, an alkane-thiol, and an oligonucleotide-thiol.

4. The composition of claim 3 wherein the stabilizer is PEG.

5. The composition of claim 1 wherein the polypeptide contains from 9 amino acids to 40 amino acids.

6. The composition of claim 1 wherein the polypeptide contains from 9 amino acids to 30 amino acids.

7. The composition of claim 1 wherein the polypeptide contains from 9 amino acids to 18 amino acids.

8. The composition of claim 1 wherein the polypeptide is selected from the group consisting of RRANAALKAGELYKSILY (SEQ ID NO: 1), RRANAALKAGELYKCILY (SEQ ID NO: 2), GELYKSILY (SEQ ID NO: 3), GELYKCILY (SEQ ID NO: 4), SYIRIADTNIT (SEQ ID NO: 5), TKKTLRT (SEQ ID NO: 6), SQNPVQP (SEQ ID NO: 7), RLDGNEIKR (SEQ ID NO: 8), KELNVYT (SEQ ID NO: 9), KLWVLPK (SEQ ID NO: 10), CQDSETRTFY (SEQ ID NO: 11), AHEEISTTNEGVM (SEQ ID NO: 12), GLRSKSKKFRRPDIQYPDATDEDITSHM (SEQ ID NO: 13), GSITTIDVPWNV (SEQ ID NO: 14), and NGVFKYRPRYFLYKHAYFYPPLKRFPVQ (SEQ ID NO: 15).

9. The composition of claim 1 wherein the polypeptide is selected from the group consisting of RRANAALKAGELYKSILY (SEQ ID NO: 1), RRANAALKAGELYKCILY (SEQ ID NO: 2), GELYKSILY (SEQ ID NO: 3), GELYKCILY (SEQ ID NO: 4), SYIRIADTNIT (SEQ ID NO: 5), TKKTLRT (SEQ ID NO: 6), SQNPVQP (SEQ ID NO: 7), and RLDGNEIKR (SEQ ID NO: 8).

10. The composition of claim 1 wherein the polypeptide comprises the amino acid sequence GELYKXILY, wherein X is serine, cysteine, or threonine (SEQ ID NO: 16).

11. The composition of claim 1 wherein the polypeptide is RRANAALKAGELYKSILY (SEQ ID NO: 1).

12. The composition of claim 1 wherein the polypeptide is RRANAALKAGELYKCILY (SEQ ID NO: 2).

13. The composition of claim 1 further comprising a cysteine at the amino terminal region or carboxy terminal region.

14. The composition of claim 13 further comprising a spacer.

15. The composition of claim 14 wherein the spacer comprises at least one glycine.

16. The composition of claim 1 further comprising a peptide sequence selected from the group consisting of GC, CG, and GCG.

17. The composition of claim 1 further comprising a carrier.

18. The composition of claim 1 wherein the nanoparticle is a core plus shell nanoparticle.

* * * * *